(12) United States Patent
Archibald et al.

(10) Patent No.: US 6,541,549 B2
(45) Date of Patent: *Apr. 1, 2003

(54) NON-XENOESTROGENIC STABILIZERS FOR ORGANIC MATERIALS

(75) Inventors: Scott R. Archibald, Thomaston, CT (US); Tracy L. Coffin-Werner, Gastonia, NC (US)

(73) Assignee: Crompton Corporation, Middlebury, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/430,969

(22) Filed: Nov. 1, 1999

(65) Prior Publication Data

US 2001/0053805 A1 Dec. 20, 2001

(51) Int. Cl.[7] .............................................. C08K 5/524
(52) U.S. Cl. .................... 524/128; 524/120; 524/150; 524/151; 558/71; 558/78; 426/547
(58) Field of Search ................................. 524/120, 128, 524/150, 151; 558/71, 78; 426/547

(56) References Cited

U.S. PATENT DOCUMENTS

| | | | | |
|---|---|---|---|---|
| 3,053,878 A | * | 9/1962 | Friedman et al. | 524/120 |
| 3,305,529 A | * | 2/1967 | Fritz et al. | 524/151 |
| 3,305,608 A | * | 2/1967 | Baranauckas et al. | 524/128 |
| 3,476,699 A | * | 11/1969 | Kauder et al. | 524/128 |
| 3,662,032 A | * | 5/1972 | Kauder et al. | 524/128 |
| 4,086,304 A | * | 4/1978 | Hutton et al. | 524/120 |
| 4,094,999 A | * | 6/1978 | Cohen et al. | 426/547 |
| 4,116,926 A | * | 9/1978 | York | 524/128 |
| 4,246,170 A | * | 1/1981 | Evans | 524/128 |
| 4,290,976 A | * | 9/1981 | Hechenbleikner et al. | 524/120 |
| 4,305,866 A | * | 12/1981 | York | 524/120 |
| 4,650,894 A | * | 3/1987 | Fisch et al. | 558/71 |
| 5,290,747 A | | 3/1994 | Yuo et al. | 502/162 |
| 5,364,895 A | * | 11/1994 | Stevenson et al. | 524/120 |
| 5,532,401 A | * | 7/1996 | Stevenson et al. | 558/95 |
| 5,767,179 A | * | 6/1998 | Takado | 524/103 |
| 5,840,792 A | * | 11/1998 | Machimura et al. | 524/417 |

FOREIGN PATENT DOCUMENTS

| | | |
|---|---|---|
| DE | 2709528 | 9/1977 |
| DE | 4202276 | 8/1992 |
| DE | 19520337 | 12/1995 |
| EP | 033395 | 5/1986 |
| EP | 511156 | 10/1992 |
| EP | 511156 A2 | 10/1992 |
| EP | 518241 | 12/1992 |
| JP | 54030241 | 3/1979 |
| JP | 54041948 | 4/1979 |
| JP | 54043952 | 5/1979 |
| JP | 54163938 | 12/1979 |
| JP | 59004629 | 1/1984 |
| JP | 61113631 | 5/1986 |
| JP | 02097539 | 8/1988 |
| JP | 02225542 | 8/1988 |
| JP | 03025437 | 2/1991 |

* cited by examiner

Primary Examiner—Peter Szekely
(74) Attorney, Agent, or Firm—Michael P. Dilworth; Paul Grandinetti

(57) ABSTRACT

A non-xenoestrogenic phosphorus-containing stabilizer for organic materials is disclosed wherein the stabilizer is selected from the group consisting of phosphorus-containing compounds of the structures

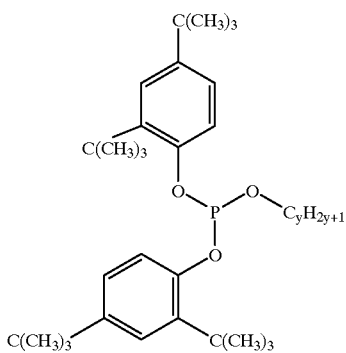

wherein y in an integer of from 6 to 20, and

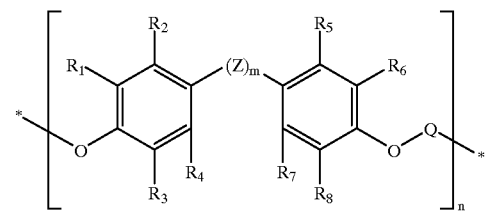

where Z is a linking group, m is 0 or 1, n is an integer of at least 2, the asterisks are independently selected terminal groups, $R_1$, $R_2$, $R_3$, $R_4$, $R_5$, $R_6$, $R_7$, and $R_8$ are independently selected from the group consisting of hydrogen, alkyl groups, aralkyl groups, or halogen groups and Q is selected from the group consisting of

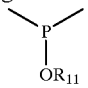

where $R_{11}$ is alkyl or aralkyl, and

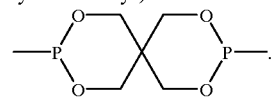

5 Claims, 1 Drawing Sheet

NON-XENOESTROGENIC STABILIZERS FOR ORGANIC MATERIALS

BACKGROUND OF THE INVENTION

1. Field of the Invention

The present invention relates to stabilizers for polymers and other organic materials. More particularly, the present invention relates to stabilizers for polymers or other organic materials that are phosphorus-containing molecules or oligomers that do not act as xenoestrogens.

2. Description of Related Art

Phosphorus-containing antioxidants, such as, phosphites, have been used as stabilizers in organic materials, such as, rubber, plastics, oils, and the like. The fourth edition of "Plastic Additives" by Gachter and Muller discusses in great detail the stabilization of plastics and polymers by commercialized phosphites, such as, tris(nonylphenyl)phosphite (TNPP) and tris(2,4-di-t-butylphenyl)phosphite. TNPP is the primary low cost liquid phosphite stabilizer used in the plastics and rubber industry. Recently, however, plastic and rubber manufacturers have been reluctant to utilize TNPP in their formulations owing to concerns that TNPP may be a xenoestrogen (foreign estrogen). Many of these concerns were raised recently in Colburn, T. et al., *Our Stolen Future*, Dutton (1996) and related articles. In this regard, xenoestrogens are suspected of being hormonally active in developing organisms.

Non-polymeric phosphite compounds are disclosed in U.S. Pat. No. 5,290,747 as primary catalysts for the formation of Nylon 6. The generic structures of these disclosed phosphites are represented by generic structure I (where n>5).

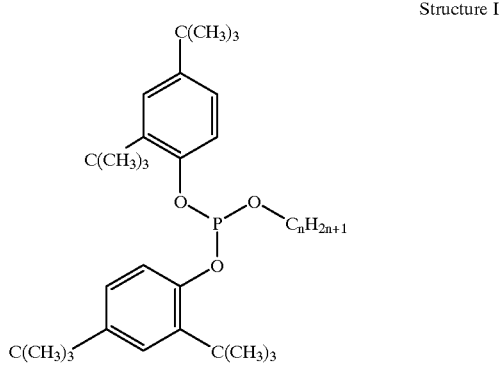

Structure I

With regard to non-polymeric phosphite stabilizers, two general classes of phosphites known in the prior art can be represented by structures II and III.

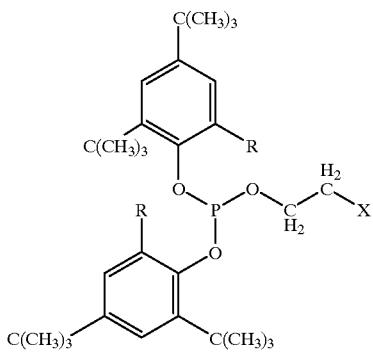

Structure II wherein R is H or $CH_3$ and X is oxygen, sulfur, nitrogen, and the like. Included in generic structure II is commercially available Irgaphos 38 (where R=$CH_3$ and X=H) described in European Patent EP-511156A2. The authors describe the phosphites listed in this patent as stabilizers for organic materials. All the stabilizers listed in EP 511156 have structures where R is represented as a methyl group. Much of the variation of the group X includes functionalized heteroatoms, such as, nitrogen, sulfur, oxygen, or functional groups such as cyano, trifluoromethyl, hindered amines, etc. The authors also describe structures wherein R=$CH_3$ and X is an alkyl or aralkyl group.

Japanese Patent 54163938 describes the improved thermal stability of PVC and ABS polymers containing compounds of structure II where R=H and X is an ethylene glycol.

Japanese Patent 55000747 describes a similar composition wherein R=$CH_3$.

German patent DE2709528 describes a stabilizer for plastics, such as, polypropylene, where R=H and X contains a second phosphite in a spiral arrangement.

British patent GB1180398 describes phosphites (where R=H and the entire group attached to X and including X is a tert-butyl group) used as thermal stabilizers for SBR or ABS rubber.

German patent DE4202276 describes a compound related to Irgaphos 38 (where R=H and X=H) that is used as a stabilizer for polyolefins.

Japanese Patent JP03025437 describes a butyl sulfone derivative (where R=H and X=$SO_2$-butyl) used in silver halide color photographic materials to prevent fading of color images.

Japanese patent JP59004629 describes a phosphite linked to another phosphite structure through an ether linkage (R=H and X=O). This phosphite is used as a photochemical and thermal stabilizer for polymer compounds.

German patent DE19520337 describes phosphite compounds (R=H, $CH_3$ and X=O) used to stabilize organic materials, such as, polyolefins, lubricants, etc. against oxidative, thermal or photochemical degradation.

A second general class of non-polymeric phosphites is represented by generic structure III. Phosphites within generic structure III are materials wherein the bis(2,4-di-tert-butylphenol)phosphite groups are joined symmetrically or non-symmetrically to a linkage group Y.

Structure III

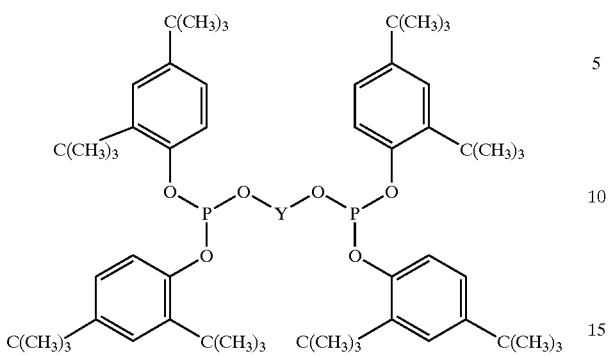

Structure III

Japanese patents 58152029, 01038456, and 02225542 describe a diphosphite derivative of III in which the phosphite moieties are linked together via a spiro ether group. These patents describe the use of this spiro ether linked diphosphite to stabilize polyolefin polymers, such as, polypropylene, used in radiation sterilizable applications.

Japanese patents JP54041948, JP54043952, and JP54030241 describe diphosphite stabilizers for polymers, such as, polypropylene, where the phosphite moieties are linked via either a bis 1,4-methylene substituted cyclohexane group or a 2,2-dimethylpropyl group. The diphosphite containing the 2,2-dimethylpropyl linkage group is also described as a chelating ligand of a hydroformylation catalyst in WO9518089 and in the above-described GB1180398 where this diphosphite is used as a thermal stabilizer for SBR or ABS rubber. Japanese patent JP61113631 describes polyolefin compositions with improved processing stability and heat resistance with the diphosphite containing the 2,2-dimethylpropyl linkage group. In addition, Japanese patent JP61113631 also describes the use of a different diphosphite with an n-hexyl group as the linking agent.

European patent EP-518241 describes a diphosphite with an unsymmetrical ethyl substituted ethylene linkage group useful as a ligand for a hydroformylation catalyst.

Japanese patent JP02097539 describes a substituted diphenol as an antioxidant for polyolefins.

European patent EP33395 describes heat and light stabilizers for polymers also based on a substituted diphenol.

SUMMARY OF THE INVENTION

The present invention is directed to liquid, non-estrogenic phosphites or polymeric phosphites that provide stabilization of organic materials that is similar to or better than that provided by TNPP.

More particularly, the present invention relates to phosphorus-containing molecules or low molecular weight phosphorus-containing polymers that act as stabilizers of organic materials and do not act as xenoestrogens. Generically, the present invention is directed to two types of related alkylated phosphite stabilizers: non-polymeric phosphites and polymeric stabilizers.

The nonestrogenic phosphite stabilizers of the present invention preferably include compounds, such as, bis(2,4-di-t-butylphenyl)octylphosphite (Stabilizer A) and the low molecular weight phosphorus-containing polymer (i.e., phosphorus-containing oligomer) poly(4,4'-{2,2'-dimethyl-5,5'-di-t-butylphenylsulfide}octylphosphite) (Stabilizer B). Stabilizers A and B have the following structures:

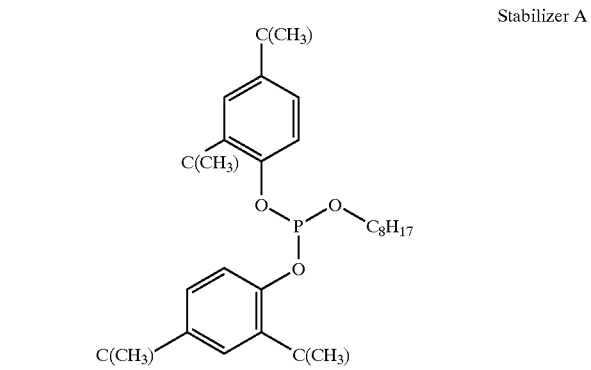

Stabilizer A

Stabilizer B

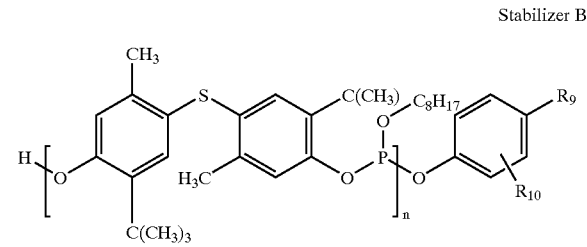

In the above formula for Stabilizer B, n is an integer of at least 2, preferably from 2 to about 6, more preferably from 2 to 4. $R_9$ and $R_{10}$ are independently selected from the group consisting of hydrogen and alkyl, preferably alkyl of from 1 to 8 carbon atoms, e.g., methyl, ethyl, propyl, butyl, pentyl, hexyl, heptyl, octyl, isomers of the foregoing, and the like. In a preferred embodiment, $R_9$ and $R_{10}$ are hydrogen.

The oligomeric non-xenoestrogenic phosphorus-containing materials are of the general structure IV:

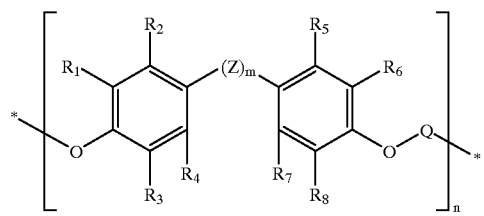

where Z is a linking group, m is 0 or 1, n is an integer of at least 2, the asterisks are independently selected terminal groups, and Q is selected from the group consisting of

where $R_{11}$ is alkyl or aralkyl, preferably having from 1 to 20 carbon atoms inclusive, more preferably 6 through 20, most preferably 6 through 10, in the alkyl moiety and from 6 to 10 carbon atoms in any aryl moiety attached thereto, and

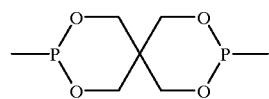

These phosphorus-containing oligomers comprise two main portions: a diphenol portion and a phosphorus portion. The diphenol portion comprises two substituted phenols that are directly linked (when m is 0) or are coupled by common linking groups (Z) for these materials (when m is 1), such as, for example, isopropylidene, hexafluoroisopropylidene, sulfur, sulfone, or oxygen. The phenol portion of the diphenol can also be substituted ($R_1$–$R_8$) with alkyl groups, aralkyl groups, or halogen groups.

More particularly, the present invention is directed to a non-xenoestrogenic phosphorus-containing stabilizer for organic materials wherein the stabilizer is selected from the group consisting of phosphorus-containing compounds of the structures

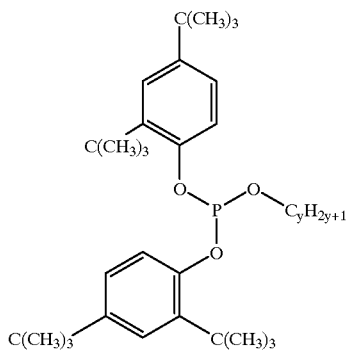

wherein y in an integer of from 6 to 20, and

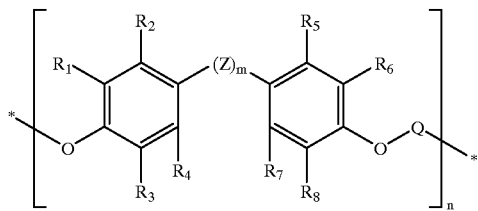

where Z is a linking group, m is 0 or 1, n is an integer of at least 2, the asterisks are independently selected terminal groups, $R_1$, $R_2$, $R_3$, $R_4$, $R_5$, $R_6$, $R_7$, and $R_8$ are independently selected from the group consisting of hydrogen, alkyl groups, aralkyl groups, or halogen groups and Q is selected from the group consisting of

where $R_{11}$ is alkyl or aralkyl, and

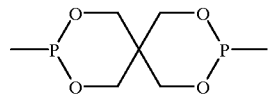

In another aspect, the present invention is directed to a method for stabilizing an organic material comprising adding to said organic material a non-xenoestrogenic, phosphorus-containing stabilizer selected from the group consisting of phosphorus-containing compounds of the structures

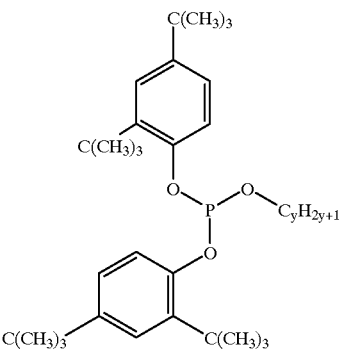

wherein y is an integer of from 6 to 20, and

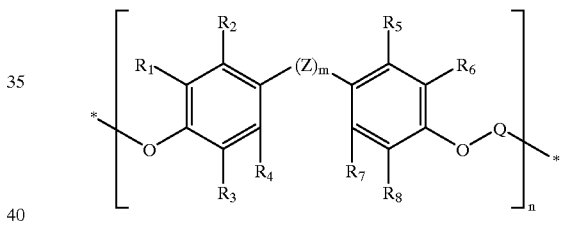

where Z is a linking group, m is 0 or 1, n is an integer of at least 2, the asterisks are independently selected terminal groups, $R_1$, $R_2$, $R_3$, $R_4$, $R_5$, $R_6$, $R_7$, and $R_8$ are independently selected from the group consisting of hydrogen, alkyl groups, aralkyl groups, or halogen groups and Q is selected from the group consisting of

where $R_{11}$ is alkyl or aralkyl, preferably having from 1 to 20 carbon atoms inclusive, preferably 6 through 20, more preferably, 6 through 10, in the alkyl moiety and from 6 to 10 carbon atoms in any aryl moiety attached thereto, and

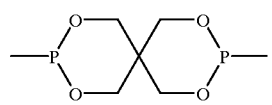

In still another aspect, the present invention is directed to a composition of matter comprising an oligomer of the structure

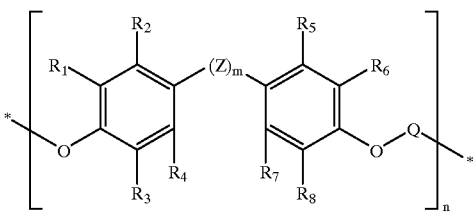

where Z is a linking group, m is 0 or 1, n is an integer of at least 2, the asterisks are independently selected terminal groups, $R_1$, $R_2$, $R_3$, $R_4$, $R_5$, $R_6$, $R_7$, and $R_8$ are independently selected from the group consisting of hydrogen, alkyl groups, aralkyl groups, or halogen groups and Q is selected from the group consisting of

where $R_{11}$ is alkyl or aralkyl, and

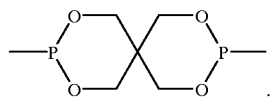

DESCRIPTION OF THE PREFERRED EMBODIMENTS

Figure 1:
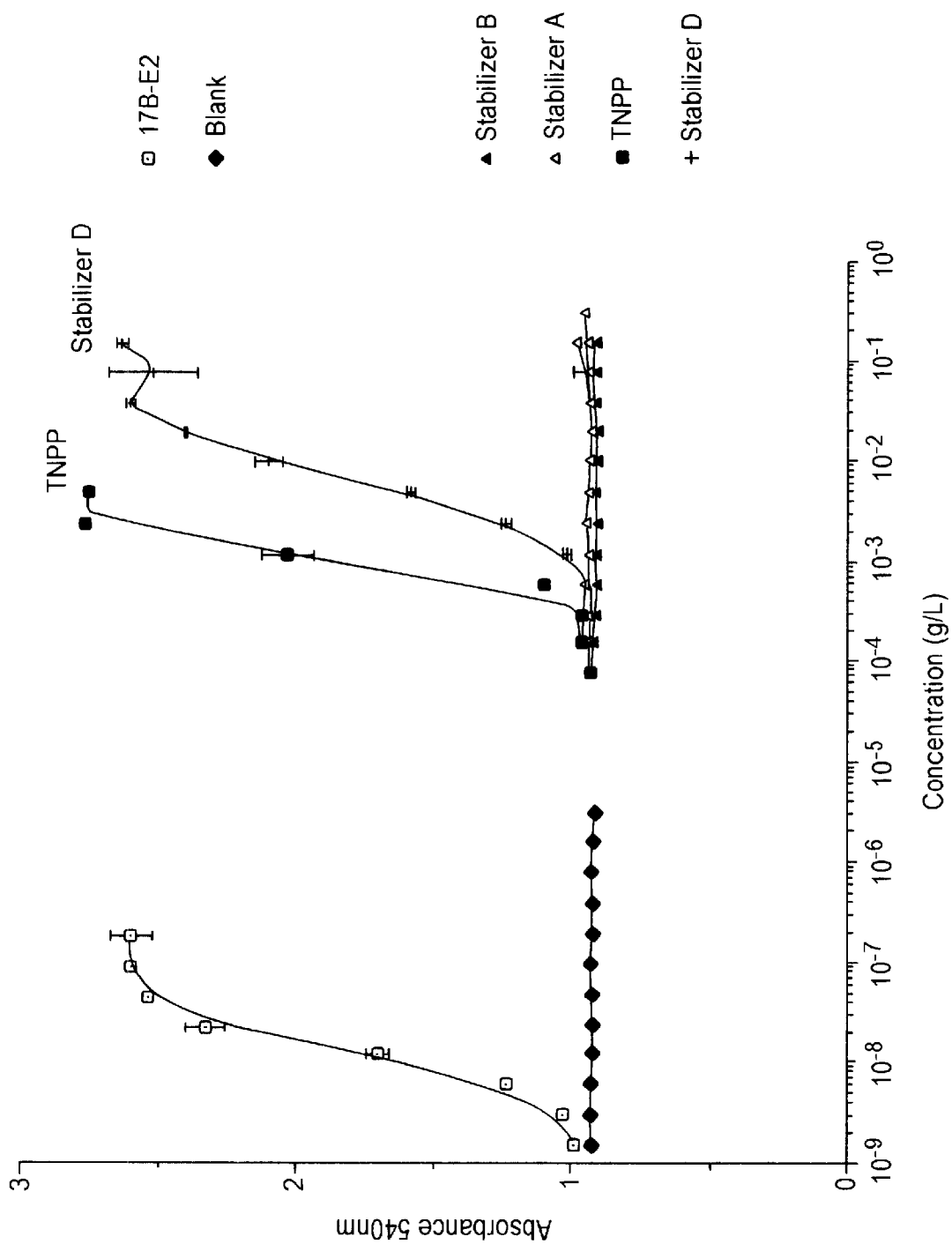
FIG. 1 is a graph showing dose-dependent responses of four parent chemicals, along with 17β-estradiol, in the yeast estrogen screen.

Organic materials, such as, rubber, plastic resins, lubricating oils, petroleum fuels, waxes, and organic liquids are well known to need protection from oxidation. Many of these materials depend on secondary antioxidants, such as, phosphites, to protect the material from oxidative degradation and discoloration.

In particular, the plastic resins can be a thermoplastic polyolefin, such as, polyethylene, polypropylene, polystyrenes, polyvinylhalides, or other thermoplastic resins, including engineering thermoplastics. Engineering thermoplastics include resins, such as, polyamides, polyesters, polyphenyleneoxides, polyphenylenesulfides, polyacetals, aliphatic polyketone co or terpolymers, poly(ethersulfones), polycarbonates, liquid crystalline polymers, poly(etheretherketones), and poly(arylates).

Rubbers include highly unsaturated polymers, such as, natural or synthetic elastomers, for example, cis-polyisoprene, polybutadiene, poly(styrene-butadiene), polychloroprene, polyacrylonitrile, and the like, as well as elastomers having lesser unsaturation, such as, EPDM, EPR, and butyl or halogenated butyl rubbers.

Lubricating oils can include lubrication oil, transmission oils, motor oils, and greases. Petroleum fuels and organic liquids can be gasoline, diesel fuel, or jet fuel.

In particular, thermoplastic polyolefins that can beneficially be stabilized against degradation by means of the compounds of the present invention include homopolymers derived from mono and di-ethylenically unsaturated hydrocarbon monomers having at least three carbon atoms, such as, polypropylene, polyisobutylene, polymethylbutene-1, polymethylpentene-1, polybutene-1, polystyrene (including polymers of styrene, such as, impact polystyrene, ABS resin or acrylonitrile/butadiene/styrene copolymer, and SBR), polyisobutylene, and the like; copolymers derived from two or more monomers such as ethylene-propylene copolymers having at least a majority of propylene, propylene-butene-1 copolymers, propylene-isobutylene copolymers, and blends of a majority of polypropylene with a minority of polyethylene, propylene, and polybutene-1, and propylene and polyisobutylene.

The foregoing polyolefin homopolymers, copolymers, and blends thereof can be combined with minor amounts by weight, i.e., less than about 50 weight percent and preferably less than 20 weight percent, of one or more compatible or compatibilized polymers other than those mentioned, for example, polyvinylhalides, chlorinated polyolefins, polyesters, polyamides, polyacrylates, and the like.

As stated above, the present invention is directed a non-xenoestrogenic phosphorus-containing stabilizer for organic materials wherein the stabilizer is selected from the group consisting of phosphorus-containing compounds of the structures

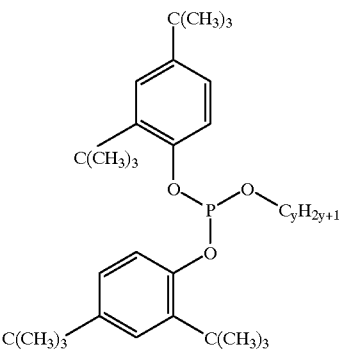

wherein y in an integer of from 6 to 20, and

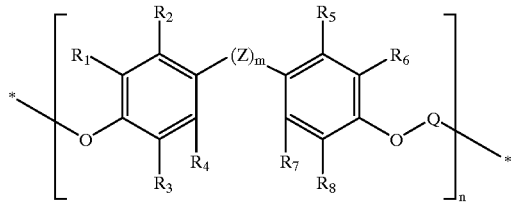

where Z is a linking group, m is 0 or 1, n is an integer of at least 2, the asterisks are independently selected terminal groups, $R_1$, $R_2$, $R_3$, $R_4$, $R_5$, R6, $R_7$, and $R_8$ are independently selected from the group consisting of hydrogen, alkyl groups, aralkyl groups, or halogen groups and Q is selected from the group consisting of

where $R_{11}$ is alkyl or aralkyl, preferably having from 1 to 20 carbon atoms inclusive, more preferably 6 through 20, most preferably 6 through 10, in the alkyl moiety and from 6 to 10 carbon atoms in any aryl moiety attached thereto, and

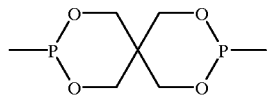

In the above structural formula, the linking group Z is preferably selected from the group consisting of alkylene, substituted alkylene, sulfur, sulfone, and oxygen.

Where Z is alkylene, it is preferably alkylene of from 1 to 20 carbon atoms, e.g., methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, isomers of the foregoing, and the like.

Where Z is a substituted alkylene, it is preferably an alkylene of from 1 to 20 carbon atoms as described above having any substituent(s) attached thereto that will not adversely affect the stabilizing properties of the compound. Preferably, such substituent(s) will be one or more halogens, e.g., fluoro, chloro, bromo, or iodo.

The coupler, Q, of the above structural formula is preferably pentaerythritol diphosphite.

The chain terminating groups of the above formula can be, for example, hydrogen on the left side of the formula and, on the right side,

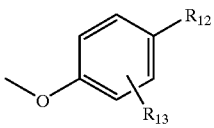

where $R_{12}$ and $R_{13}$ are independently selected from the group consisting of hydrogen and alkyl of from 1 to 8 carbon atoms. It is preferred that both $R_{12}$ and $R_{13}$ be hydrogen.

In the above formula, $R_1$, $R_2$, $R_3$, $R_4$, $R_5$, $R_6$, $R_7$, and $R_8$ are independently selected from the group consisting of hydrogen, alkyl groups, aralkyl groups, or halogen groups. Where any of $R_1$, $R_2$, $R_3$, $R_4$, $R_5$, $R_6$, $R_7$, and $R_8$ are alkyl, they are preferably alkyl of from 1 to 20 carbon atoms, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl, and isomers of the foregoing. It is more preferred that where any of $R_1$, $R_2$, $R_3$, $R_4$, $R_5$, $R_6$, $R_7$, and $R_8$ are alkyl they are alkyl of from 1 to 8 carbon atoms, most preferred that they are of from 1 to 4 carbon atoms, i.e., methyl, ethyl, propyl, isopropyl, butyl, isobutyl, sec-butyl, or tert-butyl. Where any of $R_1$, $R_2$, $R_3$, $R_4$, $R_5$, $R_6$, $R_7$, and $R_8$ are aralkyl, the alkyl moiety is preferably of from 1 to 20 carbon atoms, as described above, and the aryl moiety is preferably of from 6 to 10 carbon atoms, e.g., phenyl, naphthyl, anthracyl, phenanthryl, and the like, more preferably phenyl. Such aryl moieties can be further substituted, if desired, with additional groups that will not adversely affect the stabilizing properties of the compound. Where any of $R_1$, $R_2$, $R_3$, $R_4$, $R_5$, $R_6$, $R_7$, and $R_8$ are halogen, they are preferably fluoro, chloro, bromo, or iodo.

In the above formulae, y is an integer of from 6 to 20, preferably from 6 to 12, more preferably, from 6 to 10.

The amount of the stabilizers of the present invention incorporated into the foregoing organic materials will, at a minimum, be that required to impart a significant level of stability against oxidative degradation. In general, such amounts can vary from about 0.01 to about 5.0, and preferably from about 0.05 to 0.5, weight percent, where the organic material is a polyolefin homopolymer, copolymer, or polyolefin blend. Although amounts of the stabilizer in excess of about 5 weight percent can be employed, such amounts may have a deleterious effect on the physical and mechanical properties of the polyolefin substrate, in which case they should ordinarily be avoided.

The procedures employed to incorporate the stabilizers into an organic material are not critical and, in general, follow any of the known procedures for incorporating additives in such compositions. For example, these stabilizers can be introduced into a polyolefin and homogeneously distributed throughout the polymer by milling, extrusion blending, or other mechanical working procedure. The stabilizer can be added to the polyolefin by way of a preconcentrate or in a carrier system, for example, in a suitable solvent or co-solvent.

Following common practice, other additives can be introduced into the organic material prior to, during, and/or following addition of the stabilizer. The additives of this invention can be used in combination or with other additives typically found in organic materials. These additives can be primary antioxidants, such as, hindered phenols, amine antioxidants, other secondary antioxidants, such as, thioesters, or processing agents, metal deactivators, light stabilizers, fillers, antistatic agents, colorants, reinforcements, lubricants, plasticizers, and the like, present in their customary amounts.

Examples of antioxidants that can be used with the stabilizers of the present invention include, but are not limited to, 2,6-di-tert.-butyl-4-methylphenol, 2-tert-butyl-4, 6-dimethylphenol, 2,6-di-tert.-butyl-4-methoxymethylphenol, 2,6-dioctadecyl-4-methylphenol, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate, bis-(3, 5-di-tert.-butyl-4-hydroxyphenyl) adipate, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3, 6-di-sec.-amylphenol), 4,4'-thio-bis-(6-tert.-butyl-2-methylphenol), 4,4'-bis-(2,6-dimethyl-4-hydroxyphenyl) disulphide, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(.alpha.-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1, 5,5-tetra-(5-tert.-butyl-4-hydroxy-2-methylphenyl)-pentane, ethylene glycol bis-(3,3-bis-(3'-tert.-butyl-4'-hydroxyphenyl)-butyrate), octadecyl 4-hydroxy-3,5-dimethylbenzyl mercaptoacetate, tris-(3,5-di-tert.-butyl-4-hydroxybenzyl)amine, bis-(4-tert.-butyl-3-hydroxy-2,6-dimethylbenzyl) dithioterephthalate, dioctadecyl 2,2-bis-(3, 5-di-tert.-butyl-2-hydroxybenzyl)-malonates, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate, di-(4-(1,1,3,3-tetramethyl) phenyl)2,2-bis-(3,5-di-tert.-butyl-4-hydroxybenzyl)-malonate, 1,3,5-tri-(3,5-di-tert.-butyl-4-hydroxybenzyl)-2,4, 6-trimethylbenzene, 1,4-di-(3,5-di-tert.-butyl-4- hydroxybenzyl)-2,3,5,6-tetramethylbenzene, 2,4,6-tri-(3,5-di-tert.-butyl-4-hydroxybenzyl)-phenol, 2,4-bis-octylmercapto-6-(3,5-di-tert. -butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine, 1,3,5-tris-(3,5-di-tert.-butyl-4-hydroxybenzyl) isocyanurate, 1,3,5-tris-(3, 5-di-tert.-butyl-4-hydroxyphenyl-propionyl)-hexahydro-s-triazine and N,N-di-(3,5-di-tert.-butyl-4-hydroxyphenyl-propionyl)-hexamethylenediamine, N,N'-(bis-p-(3,5-di-t-butyl-4-hydroxyphenyl)-propionyl)-hydrazine, esters of β-(3,5-di-tert.-butyl-4-hydroxyphenyl)-propionic acid, β-(5-tert.-butyl-4-hydroxy-3-methylphenyl)-propionic acid, or 3,5-di-tert.-butyl-4-hydroxyphenylacetic acid with monohydric or polyhydric alcohols, dimethyl 3,5-di-tert.-butyl-4-hydroxybenzyl-phosphonate, diethyl 3,5-di-tert.-butyl-4-hydroxybenzyl-phosphonate dioctadecyl 3,5-di-tert.-butyl-4-hydroxybenzyl-phosphonate, and dioctadecyl 5-tert.-butyl-4-hydroxy-3-methylbenzylphosphonate.

Examples of further additives that can be used together with the stabilizers of the present invention include, but are not limited to:

aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline, octylated diphenylamine, nonylated diphenylamine, N-phenyl-N'-cyclohexyl-p-phenylenediamine, N-phenyl-N'-isopropyl-p-phenylenediamine, N,N'-di-sect-octyl-p-phenylenediamine, N-phenyl-N'-sec.-octyl-p-phenylenediamine, N,N'-di(1,4-dimethylpenthyl)-p-phenylenediamine, N,N'-dimethyl-N,N-di-(sec.-octyl)-p-phenylenediamine, 2,6-dimethyl-4-methoxyaniline, 4-ethoxy-N-sec.-butylaniline, di-phenylamineacetone condensation product, aldol-1-naphthylamine and phenothiazine; UV-absorbers and light-stabilizing agents, such as, 2-(2'-hydroxyphenyl)-benzotriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or-2-methyl-4,6-di-tert.-butylester, acrylates, e.g. α-cyano-β,β-diphenylacrylic acid-ethyl ester or -isooctyl ester, α-carbomethoxy-cinnamic acid methyl ester, α-cyano-β-methyl-p-methoxycinnamic acid methyl ester or -butyl ester or N-(β-carbomethoxyvinyl)-2-methyl-indoline, sterically hindered amines, e.g. 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,3,8-tetramethyl-1,3,8-triazaspiro(4,5)decane-2,4-dione, oxalic acid diamides, e.g. 4,4'-di-octyloxy-oxanilide, 2,2'-di-octyloxy-5,5'-di-tert.-butyl-oxanolide. 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and the mixtures thereof with 2-ethoxy-2'-ethyl-5,4'-di-tert.-butyl-oxanilide, or mixtures of ortho- and paramethoxy- as well as of o- and p-ethoxy-disubstituted oxanilides;

metal deactivators, e.g., oxanilide, isophthalic acid dihyrazide, sebacic acid-bis-phenylhydrazide, bis-benzylidene-oxalic acid dihydrazide, N,N'-diacetal-adipicaciddihydrazide, N,N'-bis-salicyloyloxalic acid dihydrazide, N,N'-bis-salicyloylhydrazine, N,N'-bis(3,5-di-tert.-butyl-4-hydroxyphenylpropionyl)hydrazine, N-salicyloyl-N'-salicylalhydrazine, 3-salicyloylamino-1,2,4-triazole or N,N'-bis-salicyloyl-thiopropionic acid dihydrazide;

basic co-stabilizers, e.g., alkali metal salts and alkaline-earth metal salts of higher fatty acids, e.g., Ca-stearate, Zn-stearate, Mg-behenate, Na-ricinoleate or K-palmitate; nucleation agents, e.g., 4-tert.-butylbenzoic acid, adipic acid or diphenylacetic acid; phosphites, e.g., triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa 3,9-diphospha (5,5)-undecane and tri-(4-hydroxy-3,5-di-tert.butylphenyl) phosphite.

Other additives that can be incorporated in the stabilized compositions are thiosynergists, such as, dilaurylthiodipropionate or distearylthiodipropionate, lubricants, such as, stearyl alcohol, fillers, carbon black, asbestos, lanolin, talc, glass fibers, pigments, optical brighteners, fireproofing agents, and antistatic agents.

The advantages and the important features of the present invention will be more apparent from the following examples.

EXAMPLES

Example 1

Synthesis of Octylphosphorodichloridite

Freshly distilled phosphorus trichloride (45.6 g, 0.338 mole) was charged into a four-necked round bottom flask equipped with a mechanical stirrer, an addition funnel, a thermometer, and a reflux condenser itself topped with a discharge tube. The discharge tube led to an aqueous sodium hydroxide trap for absorption of hydrogen chloride that evolves from the reaction. After cooling the reaction vessel to 0° C. with continual purging of dry nitrogen, anhydrous octanol (22 g, 0.168 mole) was added dropwise to the reaction mixture. When the addition of the octanol was complete, the reaction mixture was allowed to warm gradually up to room temperature and was then poured into a dry distillation flask. The material was distilled with a bath temperature of 80–85° C. and using a water pump vacuum to remove residual hydrogen chloride and excess phosphorus trichloride. The residue was then fractionated at 8 mm Hg to yield the product at 113–130° C. in 69% conversion. The phosphorus-31 NMR showed a peak at 176 ppm. The refractive index at 21.5° C. was 1.4682.

Example 2

Synthesis of Bis(2,4-di-t-butylphenyl)octylphosphite

Stabilizer A

Anhydrous benzene (165 mL), 2,4-di-t-butylphenol (41.2 g) and anhydrous triethylamine (21.0 g, 28.7 mL, 34% excess) was charged into a three necked flask, equipped with a mechanical stirrer, reflux condenser and thermometer. After heating the reaction mixture to 35–40° C., 23.1 g of the octylphosphorodichloridite of Example 1 was added. The reaction was heated to 80–85° C. and the reaction mixture was stirred for four hours. The hydrochloride salt of the triethylamine precipitated and was filtered off on a hot funnel and washed with hot benzene. Benzene and excess triethylamine were removed from the filtrate under vacuum. The residue was a mobile, turbid, slightly yellowish product that was again filtered through a hot funnel to remove the small quantity of precipitated salt of triethylamine. The now transparent reaction mass was treated under vacuum at a temperature of 80–85° C. and a pressure of 8–10 mm Hg for 1.5–2 hours. The small quantity of precipitated salt of triethylamine was once again filtered off with a funnel leaving a transparent, viscous product of slightly yellowish color. The phosphorus-31 NMR showed a peak at 124 ppm.

Example 3

Synthesis of Poly(4,4'-{2,2'-dimethyl-5,5'-di-t-butylphenylsulfide}octylphosphite)

Stabilizer B

To a round bottom flask was added 34.6 g (0.1 mol) of diphenyl-(2-ethylhexyl)phosphite, 35.8 g (0.1 mol) of 4,4'-thiobis (3-methyl-6-tert-butylphenol), and a catalytic quantity of metallic sodium (or alcoholate of an alkali metal). The mixture was heated at 180° C. under an atmosphere of nitrogen for one hour. The temperature was reduced to 90–100° C. and the phenol was removed under vacuum (10 mm) over 2.5 hours. When the residual pressure dropped to 1 mm, the reaction mass was subjected to vacuum for two more hours. The residual transparent glassy resin was then ground into a powder. MP=62° C. The yield was quantitative. The phosphorus-31 NMR showed a series of peaks from 126 to 131 ppm.

$MW_{meas.}$ (cryoscopic in benzene)=1680, n=3, %P 5.63; %S 5.57.

$MW_{calc.}$=1642; %P 5.66; %S 5.84

Syntheses of all polyphosphites are carried out by the poly-transesterification reaction of alkyldiphenyl-phosphite or triphenylphosphite or an appropriate bis-phenol. If the initial bis-phenol does not contain alkyl substituents in the phenolic nucleus, the poly-transesterification reaction proceeds in the absence of catalysts.

Example 4

Synthesis of Poly(4,4'-{isopropylidenediphenol}-octylphosphite)

Stabilizer C

In a round bottom flask, 34.6 g (0.1 mol) of diphenyl-(2-ethylhexyl)phosphite, 22.8 g (0.1 mol) of bisphenol-A, and a catalytic quantity of metallic sodium (or alcoholate of an alkali metal) was heated at 180° C. under an atmosphere of nitrogen for one hour. The temperature was reduced to 90–100° C. The phenol was then removed under vacuum (10 mm) over 2.5 hours. When the residual pressure dropped to 1 mm, the reaction mass was subjected to vacuum for two more hours. The yield was quantitative. The phosphorus-31 NMR showed a series of peaks from 126 to 131 ppm.

Example 5

Synthesis of Poly(4,4'-{isopropylidenebis[2,6-dibromophenol]}-octylphosphite)

Stabilizer D

In a round bottom flask, 34.6 g (0.1 mol) of diphenyl (2-ethylhexyl) phosphite, 54.4 g (0.1 mol) of teterabromodiphenylpropane, and a catalytic quantity of metallic sodium was heated for 1 hour under vacuum (9 mm) at 120° C. The phenol was removed over 6 hours as the temperature gradually was raised up to 190° C. For complete stripping of phenol, the pressure was brought to 1 mm. The residue after stripping of the phenol was ground into a light yellow powder that melted at 64° C.

$MW_{meas.}$ (cryoscopic)=1510, %P 3.8.

$MW_{calc.}$=1437 (n~2), %P 4.1.

Example 6

Synthesis of Poly(4,4'-{2,2'-dimethyl-5,5'-di-t-butylphenylsulfide}-pentaerythrityl diphosphite)

Stabilizer E

A flask containing 13.6 g (0.1 mol) of pentaerythritol and 62.0 g (0.2 mol) of triphenylphosphite was heated under vacuum (8–10 mm Hg) at 90–95° C. for one hour to strip off phenol. Gradually the temperature was raised to 170° C., and the pressure was reduced to 1 mm Hg. The remaining residue was diphenylpentaerythrityldiphosphite.

The diphenylpentaerythrityldiphosphite thus obtained was mixed with 35.8 g (0.1 mol) 4,4'-thiobis(3-methyl-6-tert-butylphenol). The thiobisphenol was melted into the diphosphite under a vacuum (8–10 mm) while the phenol was removed. The temperature was gradually raised from 100 to 175° C. Any residual phenol was removed at 1 mm Hg. The resulting product was transparent and glass-like and was ground into a white powder. The phosphorus-31 NMR showed a series of peaks from 85 to 132 ppm. $T_m$=69° C.

$MW_{meas.}$ 1120. (n~2). %P 11.03; %S 5.06.

$MW_{calc.}$ 1194; %P 10.76; %S 5.36

Example 7

Xenoestrogenicity Testing

To determine the relative "endocrine" activity of several phosphite stabilizers, each was evaluated for biological activity in an in vitro assay developed to assess estrogenicity.

The assay employs a genetically engineered (recombinant) strain of yeast that generates and releases the enzyme β-galactosidase in the presence of β-17 estradiol (estrogen) or a xenoestrogen. In the culture medium, β-galactosidase is broken down to the chromogenic substrate chlorophenol red-β-D-galactopyranoside (CPRG). The activity and relative potency of xenoestrogen is determined spectrophotometrically. Full details of the assay have been discussed previously (Routledge, E. J. et al., *Environ. Tox. & Chem.* 15(3):241–248 (1996)).

FIG. 1 shows the relative "estrogenic" activity of several structurally related phosphite stabilizers.

Example 8

Tables 1–12 detail the performance of the Stabilizers A–E in polyolefins. These compounds show performance as plastic stabilizers that is comparable to or better than that of TNPP. With regard to Melt Flow Rate (MFR), a good plastic stabilizer will contribute to a low initial MFR and then maintain the low MFR. For Hunter b Color performance, a good plastic stabilizer will yield low initial color and then maintain that low color. For Long Term Heat Aging (LTHA) and Oxidative Induction Time (OIT), a good stabilizer will have a longer LTHA and OIT value.

Sample Preparation

The polyolefin powder (polyethylene or polypropylene) is dry blended with the stabilizer formulation using a typical household mixer. The mixer is run at approximately 60 rpm or a speed which does not cause the material to splash out of the bowl for at least 15 minutes. The masterbatch is then added to a preheated single screw extruder where the plastic is homogeneously mixed. Extrusion is typically performed at 200° C. for polyethylene and 250° C. for polypropylene. The extruded plastic is cooled into a cold water bath, completely dried, and pelletized. The collected polymer pellets are the result of the first pass extrusion and are the starting material for all subsequent test protocols. The isolated pellets are added to the extruder repeatedly to generate the third and fifth pass material.

Melt Flow Rate Analysis

The melt flow rate was performed using the ASTM 1238-90b test method measured at 2.16 Kg/230° C. The melt flow rate was completed on either an IIRT-M2 or Tinius Olsen extrusion plastometer.

Color Analysis

Color analysis was performed on compression molded films or plaques with either a Hunter Lab Ultrascan XE or Datacolour machine. Observations were made with a D65 illuminant and 10° observer. Yellowness Index measurements were made in accord with ASTM D 1925-70 and Hunter b Color measurements were calculated using formulas in ASTM D1925-77.

Long Term Heat Aging

Heat aging was performed based on methods in ASTM D3045-92 using a circulating air oven. The oven temperature is typically set at 90° C. for polyethylene and 140° C. for polypropylene. The samples were checked daily for degradation based on yellowing, brittleness, or crumbling.

Oxidative Induction Times

The antioxidant properties of the novel product in a fully formulated plastic are determined in the Oxidation Induction Time (OIT) test under ASTM D3895 conditions. The test is performed at 200° C. for polyethylene and 180° C. for polypropylene. Circular disks are cut from 0.25 mm films of the material to be tested and placed in aluminum pans for use in a Perkin-Elmer DSC-2C differential scanning calorimeter (DSC). The test chamber of the DSC calorimeter is purged with nitrogen during conditioning to an isocratic temperature at 200° C. (or 180° C. for PP). Conditioning is followed by immediate change to oxygen at a flow rate of 20 cc's per minute to induce thermal oxidative degradation. OIT is the time span in minutes between reaching an isocratic temperature when the oxygen environment is introduced and the time at which the DSC detects the onset of oxidation. In the OIT test, a longer OIT value indicates better oxidative stability of the formulation and the results are the average of at least three tests.

In the following tables, BHT is 2,6-di-t-butyl-4-methyl phenol (i.e., butylated hydroxy toluene) and Naugard 10 is tetrakis{methylene(3,5-di-t-butyl-4-hydroxy-hydrocinnamate)}methane.

TABLE 1

Melt Flow Rate
Polypropylene with 0.05% Calcium Stearate

| Stabilizer (0.2%) | Phenolic (0.1%) | First Pass | Third Pass | Fifth Pass |
|---|---|---|---|---|
| None | Naugard 10 | 3.5 | 4.0 | 4.5 |
| TNPP | Naugard 10 | 3.1 | 3.3 | 3.6 |

TABLE 1-continued

Melt Flow Rate
Polypropylene with 0.05% Calcium Stearate

| Stabilizer (0.2%) | Phenolic (0.1%) | First Pass | Third Pass | Fifth Pass |
|---|---|---|---|---|
| B | Naugard 10 | 3.0 | 3.1 | 3.2 |
| E | Naugard 10 | 3.1 | 3.2 | 3.4 |
| D | Naugard 10 | 3.6 | 4.1 | 4.7 |

TABLE 2

Yellowness Index
Polypropylene with 0.05% Calcium Stearate

| Stabilizer (0.2%) | Phenolic (0.1%) | First Pass | Third Pass | Fifth Pass |
|---|---|---|---|---|
| None | Naugard 10 | 13 | 19 | 26 |
| TNPP | Naugard 10 | 13 | 18 | 25 |
| B | Naugard 10 | 13 | 19 | 24 |
| E | Naugard 10 | 13 | 19 | 25 |
| D | Naugard 10 | 13 | 17 | 23 |

TABLE 3

Polypropylene with 0.05% Calcium Stearate

| Stabilizer (0.2%) | Phenolic (0.1%) | LTHA (days) | OIT @ 180° C. (min) |
|---|---|---|---|
| None | Naugard 10 | 58 | 44 |
| TNPP | Naugard 10 | 66 | 209 |
| B | Naugard 10 | 58 | 648 |
| E | Naugard 10 | 73 | 270 |
| D | Naugard 10 | 65 | 44 |

TABLE 4

Melt Flow Rate
Polypropylene with 0.05% Calcium Stearate

| Stabilizer (0.05%) | Phenolic (0.05%) | First Pass | Third Pass | Fifth Pass |
|---|---|---|---|---|
| None | BHT | 5.69 | 6.46 | 7.29 |
| TNPP | BHT | 4.87 | 5.48 | 6.32 |
| C | BHT | 4.54 | 5.24 | 5.81 |

TABLE 5

Hunter b color
Polypropylene with 0.05% Calcium Stearate

| Stabilizer (0.05%) | Phenolic (0.05%) | First Pass | Third Pass | Fifth Pass |
|---|---|---|---|---|
| None | BHT | 1.26 | 1.57 | 1.98 |
| TNPP | BHT | 1.13 | 1.52 | 1.88 |
| C | BHT | 1.06 | 1.25 | 1.53 |

TABLE 6

Polypropylene with 0.05% Calcium Stearate

| Stabilizer (0.05%) | Phenolic (0.05%) | LTHA (days) |
|---|---|---|
| None | Naugard 10 | 20 |
| TNPP | Naugard 10 | 27 |
| C | Naugard 10 | 31 |

TABLE 7

Melt Flow Rate
Polypropylene with 0.05% Calcium Stearate

| Stabilizer (0.2%) | Phenolic (0.1%) | First Pass | Third Pass | Fifth Pass |
|---|---|---|---|---|
| None | BHT | 5.45 | 5.95 | 6.84 |
| TNPP | BHT | 4.47 | 5.02 | 5.60 |
| A | BHT | 3.73 | 4.21 | 4.67 |

TABLE 8

Hunter b Color
Polypropylene with 0.05% Calcium Stearate

| Stabilizer (0.2%) | Phenolic (0.1%) | First Pass | Third Pass | Fifth Pass |
|---|---|---|---|---|
| None | BHT | 1.40 | 1.84 | 2.72 |
| TNPP | BHT | 1.35 | 1.50 | 1.77 |
| A | BHT | 1.37 | 1.43 | 1.59 |

TABLE 9

Polypropylene with 0.05% Calcium Stearate

| Stabilizer (0.2%) | Phenolic (0.1%) | LTHA (days) | OIT @ 180° C. (min) |
|---|---|---|---|
| None | Naugard 10 | 36 | 25 |
| TNPP | Naugard 10 | 50 | 73 |
| A | Naugard 10 | 42 | 153 |

TABLE 10

Melt Flow Rate
Polyethylene

| Stabilizer (0.2%) | Phenolic (0.1%) | First Pass | Third Pass | Fifth Pass |
|---|---|---|---|---|
| None | Naugard 10 | 1.0245 | 1.0512 | 1.0845 |
| TNPP | Naugard 10 | 1.0293 | 1.0631 | 1.0899 |
| A | Naugard 10 | 1.0427 | 1.0586 | 1.0698 |

TABLE 11

Hunter b Color
Polyethylene

| Stabilizer (0.2%) | Phenolic (0.1%) | First Pass | Third Pass | Fifth Pass |
|---|---|---|---|---|
| None | Naugard 10 | 0.85 | 2.01 | 2.58 |
| TNPP | Naugard 10 | −0.41 | −0.18 | −0.13 |
| A | Naugard 10 | −0.45 | −0.43 | −0.30 |

TABLE 12

Polyethylene

| Stabilizer (0.2%) | Phenolic (0.1%) | OIT @ 200° C. (min) |
|---|---|---|
| None | Naugard 10 | 18 |
| TNPP | Naugard 10 | 53 |
| A | Naugard 10 | 122 |

In view of the many changes and modifications that can be made without departing from principles underlying the invention, reference should be made to the appended claims for an understanding of the scope of the protection afforded the invention.

What is claimed is:

1. A method for stabilizing a thermoplastic polyolefin comprising adding to said polyolefin a non-xenoestrogenic, phosphorus-containing stabilizer of the structure

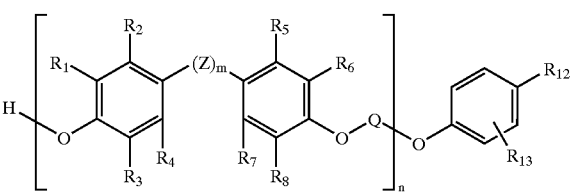

where Z is selected from the group consisting of sulfur and sulfone, m is 0 or 1, n is an integer of at least 2, $R_{12}$ and $R_{13}$ are independently selected from the group consisting of hydrogen and alkyl of from 1 to 8 carbon atoms, $R_1$, $R_2$, $R_3$, $R_4$, $R_5$, $R_6$, $R_7$, and $R_8$ are independently selected from the group consisting of hydrogen, alkyl groups, aralkyl groups of from 1 to 8 carbon atoms, or halogen groups and Q is

where $R_{11}$ is alkyl or aralkyl.

2. The method of claim 1 wherein the stabilizer is poly(4,4'-{2,2'-dimethyl-5,5'-di-t-butylphenylsulfide}octylphosphite).

3. The method of claim 2 wherein the thermoplastic polyolefin is polyethylene or polypropylene.

4. The method of claim 1 wherein the thermoplastic polyolefin is polyethylene or polypropylene.

5. Poly(4,4'-{2,2'-dimethyl-5,5'-di-t-butylphenylsultide}octylphosphite).

* * * * *